US008508106B2

(12) United States Patent
Bauer

(10) Patent No.: US 8,508,106 B2

(45) Date of Patent: Aug. 13, 2013

(54) ELECTROACOUSTIC TRANSDUCER

(75) Inventor: Edgar Bauer, Kraichtal (DE)

(73) Assignee: Richard Wolf GmbH, Knittlingen (DE)

( * ) Notice: Subject to any disclaimer, the term of this patent is extended or adjusted under 35 U.S.C. 154(b) by 372 days.

(21) Appl. No.: 12/902,297

(22) Filed: Oct. 12, 2010

(65) Prior Publication Data

US 2011/0092861 A1 Apr. 21, 2011

(30) Foreign Application Priority Data

Oct. 15, 2009 (DE) ......................... 10 2009 049 487

(51) Int. Cl.
*H01L 41/08* (2006.01)
*A61B 8/00* (2006.01)

(52) U.S. Cl.
USPC ................ 310/334; 601/2; 600/459; 367/153

(58) Field of Classification Search
USPC ..................... 310/326, 327, 334, 369; 601/2; 600/459; 367/153
See application file for complete search history.

(56) References Cited

U.S. PATENT DOCUMENTS 4,281,550 A * 8/1981 Erikson .......................... 73/626
4,721,106 A 1/1988 Kurtze et al.
4,858,597 A 8/1989 Kurtze et al.
5,111,805 A * 5/1992 Jaggy et al. ...................... 601/4
5,193,527 A * 3/1993 Schafer ........................... 601/2
6,030,346 A * 2/2000 Buck et al. ................... 600/459
6,111,967 A * 8/2000 Face et al. .................... 381/190
6,231,529 B1 * 5/2001 Bauer et al. ...................... 601/4
6,471,662 B1 * 10/2002 Jaggy et al. ...................... 601/2
6,613,005 B1 * 9/2003 Friedman et al. ................ 601/2
7,399,284 B2 * 7/2008 Miwa et al. ....................... 601/2
2001/0005417 A1 * 6/2001 Djahansouzi ................ 381/152
2006/0184072 A1 * 8/2006 Manna ............................. 601/2

FOREIGN PATENT DOCUMENTS

DE 33 19 871 A1 12/1984
DE 34 25 992 A1 1/1986
DE 39 40 808 C2 10/1991
DE 196 24 443 A1 1/1998
DE 10321578 A1 * 12/2004

OTHER PUBLICATIONS

Office Action Issued Mar. 23, 2010 in German Appln. U.S. Appl. No. 10 2009 049 487.1.

* cited by examiner

*Primary Examiner* — Thomas Dougherty
(74) *Attorney, Agent, or Firm* — Panitch Schwarze Belisario & Nadel LLP

(57) ABSTRACT

An electroacoustic transducer is provided, particularly for use in an apparatus for medical shock-wave treatment. The transducer includes several piezoelements arranged next to one another, which are embedded in a composite mass in a carrier-free manner.

17 Claims, 2 Drawing Sheets

Fig.3
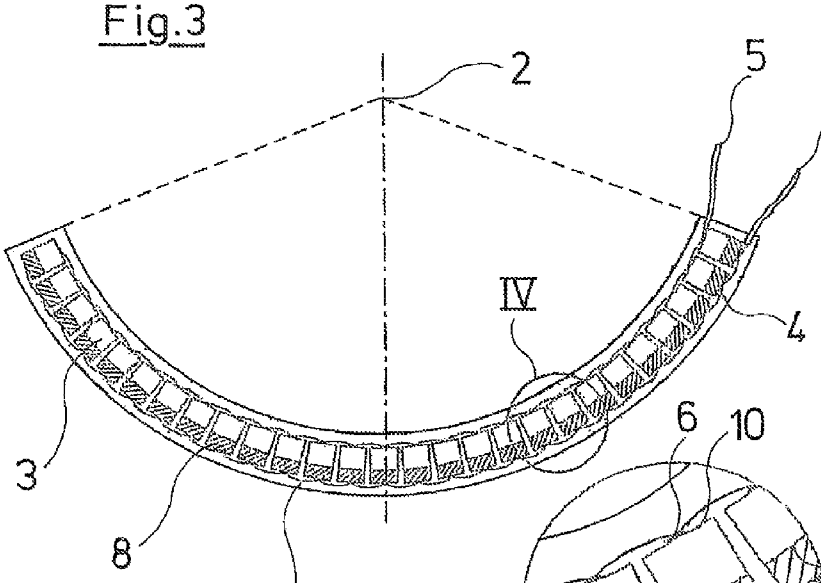
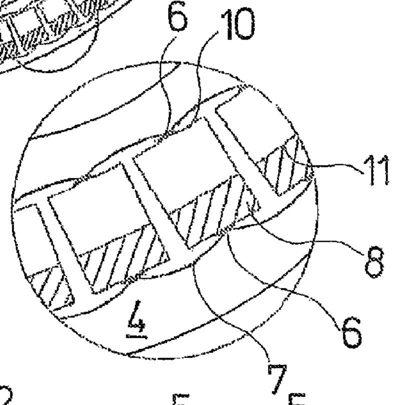
Fig.4
Fig.5
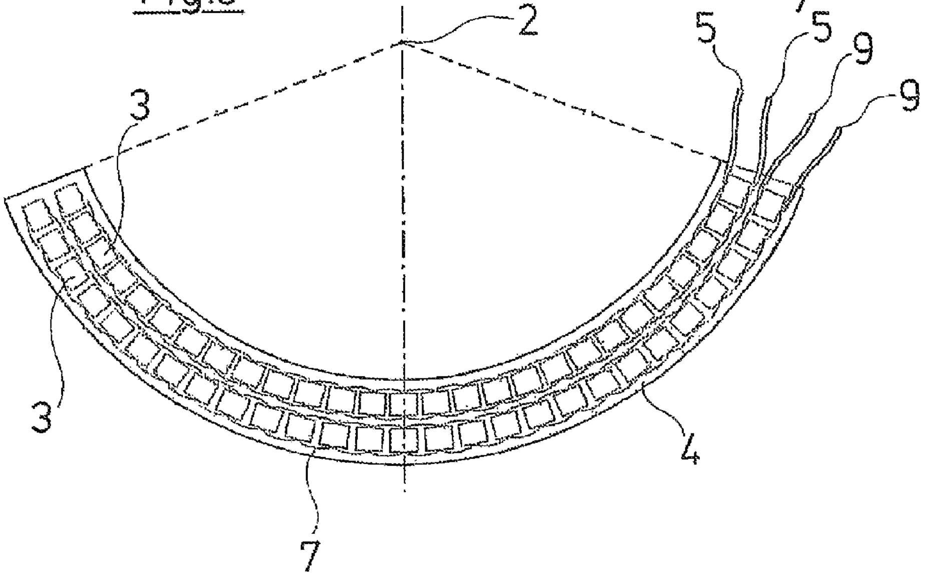

ELECTROACOUSTIC TRANSDUCER

BACKGROUND OF THE INVENTION

The invention relates to an electroacoustic transducer, in particular for use in an apparatus for medical shock-wave treatment, in which the transducer has a plurality of piezoelements arranged next to one another.

Such electroacoustic transducers are part of the state of the art and are used for example in lithotripters, such as for non-invasive treatment of stone problems. Medical shock-wave treatment apparatus meanwhile are very widespread in the medical field and are also applied for numerous other therapy purposes. Various physical principles are known for the production of shock waves. The subject matter of the present invention involves those apparatus which operate according to the piezoelectric principle, which means they have an electroacoustic transducer which is constructed from a multitude of piezoelements, also referred to as piezoelectric elements.

Such electroacoustic transducers are often designed as self-focussing transducer calottes. With such transducer calottes, a multitude of piezoelements are bonded in an electrically conductive manner, for example on a hemispherical metal calotte as a carrier, and are embedded into an elastic, electrically insulating cast mass of epoxy resin. The electrical connection of the piezoelements, which are to be connected in parallel, is thereby effected on the one hand via the metal calotte and on the other hand via a wiring on the other side of the piezoelements. Such a construction of an electroacoustic transducer is known for example from German published patent application DE 196 24 443 A1.

The electroacoustic transducer forms the core piece of the lithotripter. Since it requires much effort with regard to manufacture and is thus expensive, one strives to construct these transducers such that, apart from its good therapeutic characteristics, it also has a life duration as long as possible. The life duration of such an electroacoustic transducer functioning in a piezoelectric manner is typically limited by two causes, on the one hand by the high-voltage arc-overs at the piezoelement, which destroy the element within a short time and also damage adjacent elements as well as their insulation, and on the other hand by the fact that the piezoelements detach from the carrier calotte, which first leads to a reduction of the power, but with continued operation of the transducer leads to a fracture formation within the piezoelement and finally to a high-voltage arc-over.

While the high-voltage arc-overs due to faulty piezoelements occur practically independently of the operating time and tend rather to be the exception, detachment of the piezoelements from the carrier calotte is greatly dependent on the operating time of the transducer.

Although it is part of the state of the art from German published patent application DE 196 24 443 A1 to reduce the tendency for a high-voltage arc-over by a special insulation at the piezoelements, this however has no influence on the problem of detachment of the piezoelements from the carrier calotte.

The fastening of the piezoelements on the carrier calotte is known from German published patent applications DE 34 25 992 A1 and DE 33 19 871 A1. It is effected by an electrically conductive epoxide adhesive having a high silver component, by which the piezoelements are connected in an electrically conductive manner and mechanically to the metallic carrier calotte. It is indeed in this region, however, that the detachments occur with long-term loading.

BRIEF SUMMARY OF THE INVENTION

Against this background, it is an object of the present invention to design an electroacoustic transducer, which is constructed of piezoelements, such that on the one hand it operates with a high efficiency, but on the other hand is stable over the long term.

According to the invention, this object is achieved by an electroacoustic transducer, which in particular is provided and envisaged for use in an apparatus for medical shock-wave treatment, in which the transducer comprises a plurality of piezoelements arranged next to one another, and is characterized in that these piezoelements arranged next to one another are arranged in a carrier-free manner and are embedded in a composite mass.

The piezoelements thereby are integrated into the composite mass in a force-free manner. An adequate freedom of movement of the piezoelements, as is necessary when being subjected to voltage, is ensured by the flexibility of the composite mass.

The basic concept of the invention is not to use the typical metallic carrier of the transducer, but to realize this in a carrier-free manner by piezoelements embedded in a composite mass. The problem of the piezoelements detaching from the carrier may no longer occur due to the fact that the piezoelements are arranged in a carrier-free manner. The mechanical interconnection is achieved by the embedding into the composite mass, wherein advantageously a complete embedding of the piezoelements including the electrical connections is effected. For this purpose, the composite mass is to be selected such that, on the one hand, it provides an adequate mechanical support, thus ensuring a certain intrinsic stability of the transducer, but on the other hand, it is as elastic as possible, in order to endure the movement of the piezoelements without damage, given a subjection to voltage. The piezoelements which are used for the inventive transducer may be freely selected. Typically, the same or similar piezoelements as are also applied in the prior art are used, thus essentially cylindrical piezoelements, which are electrically contacted at their ends facing away from one another.

Particularly advantageously, the composite mass according to a further embodiment of the invention is formed by an elastic cast mass, which is electrically insulating and preferably surrounds the piezoelements on all sides. Such an elastic cast mass may advantageously be formed by a curing epoxy resin, but an embedding into thermoplastic plastics is likewise possible. The piezoelements are advantageously arranged with a spacing from one another, wherein the cast mass fills in the interstices formed by this spacing.

The contacting of the piezoelements with the electroacoustic transducer according to the invention is effected advantageously via electrically conductive connection wires, which are contacted respectively at the ends of the piezoelements and which electrically connect the piezoelements in parallel in a manner known per se. Thus, at least one lead pair for the connection of the electroacoustic transducer is led out of the composite mass. The electrical contacting by connection wires is particularly advantageous if the transducer is constructed in a two-layered or multi-layered manner, since then, the adjacent layers of piezoelements are not contacted via the carrier calotte, as in the prior art, but in a separate manner, whereby an electrical activation which is independent from one another is also possible. This is advantageous, since then the electroacoustic transducer may be adapted in a particularly ideal manner to the respective therapeutic purpose.

In order to prevent functional limitations from occurring due to the electrical contacting of the piezoelements, according to a further embodiment of the invention, it is advantageous to apply as thin as possible connection wires, typically with a diameter between 0.1 mm and 0.8 mm, and to integrate these likewise into the composite mass together with the piezoelements. Such a wire thickness, with the piezoelements which are typically applied for such transducers, on the one hand permits an adequate electricity supply, and on the other hand permits a good movement ability within the elastic and flexible composite mass. In order to reduce the skin effect which occurs at higher frequencies, instead of the previously mentioned wire dimensioning, one may also use a cord of woven, fine metal wires.

With electroacoustic transducers of the initially mentioned type, which comprise a metallic carrier, the carrier forms a so-called backing by which the tensile component of the shock waves may be reduced, which is advantageous for example with the destruction of stones. Such a backing, according to one advantageous further embodiment of the invention, may also be realized, in combination with the electroacoustic transducer according to the invention, by the piezoelements arranged next to one another respectively being provided with their own backing, thus with a rear-side reinforcement, wherein this rear-side reinforcement is likewise embedded into the composite mass, preferably together with the associated piezoelements and surrounded on all sides by the composite mass. The rear-side reinforcement according to the invention, in comparison to the prior art, permits a significantly more individual configuration, since the strength and shape of the backing may be designed in a practically infinite number of ways, which is different than with the prior art.

Advantageously, the rear-side reinforcement is formed by reinforcement bodies which are in each case bonded on the rear-side end of the piezoelement. Such a reinforcement body is advantageously electrically conductive, preferably formed of metal and is connected in an electrically conductive manner to a side of the associated piezoelement, specifically the rear side seen in the main radiation direction of the transducer. The electrical connection of these piezoelements may then be effected in an advantageous manner via the reinforcement body itself, preferably by contacting at the side of the reinforcement body facing away from the piezoelement. This design also has advantages with regard to manufacturing technology, since the respective piezoelement is merely to be connected to the reinforcement body, whereupon the entirety may be constructed into an electroacoustic transducer, in the same manner as is effected with piezoelements without backing.

If the reinforcement body is formed of a material which is not electrically conductive, such as glass, ceramic or a composite material for example, which may also be advantageous as the case may be, then it is useful to provide this reinforcement body with an electrically conductive layer, which is then connected to the associated piezoelement in an electrically conductive manner. The electrical connection of the piezoelement is then effected in the same manner as previously described, specifically by the piezoelement at the side, to which the reinforcement body connects, being contacted via the electrically conductive layer preferably at the side of the reinforcement body facing away from the piezoelement.

By the material and shaping of the reinforcement body, the acoustic characteristics of the transducer embodiments according to the invention may be varied in broad regions. Particularly advantageously, the reinforcement body is formed by a cylindrical, conical, truncated-cone-shaped, or hemispherical-shaped element. One may also envisage combinations, for example a cylindrical section, which connects to the piezoelement and is designed in a hemispherical manner on the distal side.

The electroacoustic transducer according to embodiments of the invention may be designed such that the piezoelements, which are arranged next to one another, lie in a plane (planar transducer). An acoustic lens is then applied if the sound waves departing from the planar transducer are then to be focussed. If however, a linear focussing is to be effected, then the piezoelements may be arranged in a spatial shape which is curved in a single-axis manner, for example in a cylinder segment. A spatial shape curved in a two-axis manner may also be realized by the piezoelements being arranged in the manner of a hemispherical calotte, in order to achieve a focussed electroacoustic effect, just as the electroacoustic transducers described initially with regard to the prior art.

The electroacoustic transducer according to the invention may thus be designed in practically any desired shape. According to a further embodiment of the invention, one also envisages arranging groups of piezoelements arranged next to one another, at a spacing behind one another and embedding them in the composite mass. Particularly advantageously there, the groups may be electrically connected independently of one another, in order thus to be able to activate the individual groups in a staggered manner with regard to time, and to be able to modulate the sound waves in a targeted manner. Thus, electroacoustic transducers may be created which, in their manner of functioning, are similar to those known from German Patent DE 197 33 233 C1.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 is a representation similar to FIG. 1 of another embodiment of a transducer according to the invention;

FIG. 4 is an enlarged detail of the circled portion IV in FIG. 3; and

FIG. 5 is a representation similar to FIG. 1 of a third embodiment of a transducer according to the invention.

DETAILED DESCRIPTION OF THE INVENTION

Figure 1:
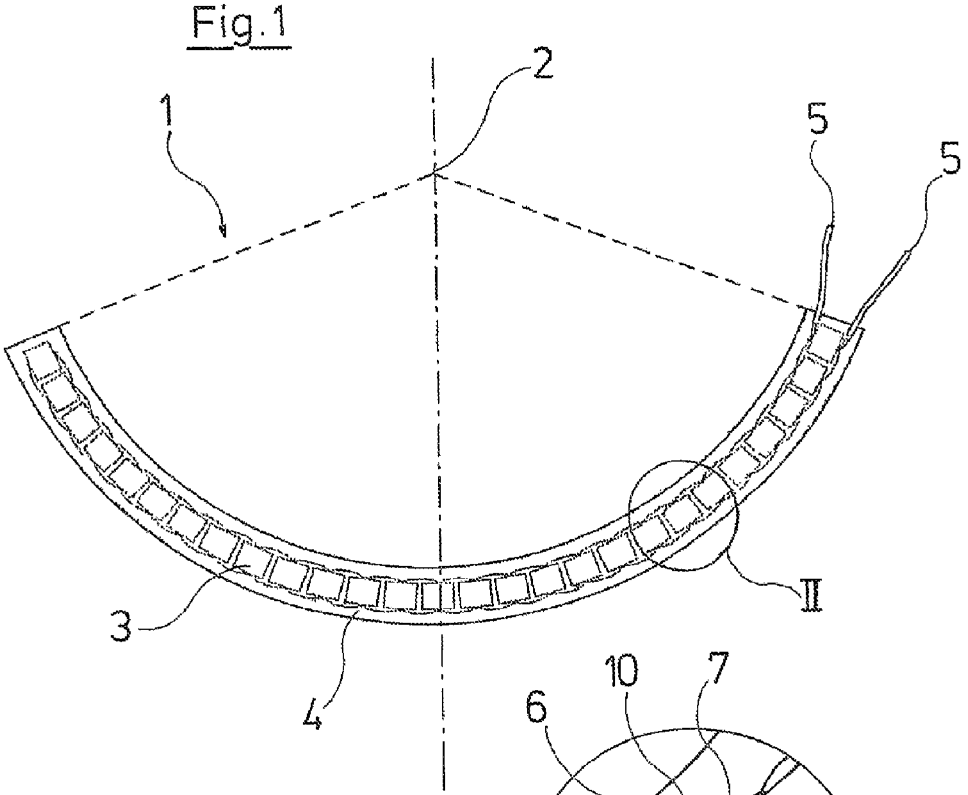
FIG. 1 is a greatly simplified schematic, sectional representation of an embodiment of a transducer according to the invention.

An electroacoustic transducer 1 is represented in FIG. 1, in the form of a self-focussing transducer calotte, as is often used with shock-wave treatment apparatus which operate according to the piezoelectric principle. The electroacoustic transducer 1 has a therapy focus 2, which is formed by the geometric middle point of the transducer calotte. This electroacoustic transducer 1 also comprises a multitude of piezoelements 3, which are arranged at a small spacing to one another and which are arranged in a carrier-free manner, such that they lie on an imagined hemispherical calotte. The piezoelements 3 are held by a composite mass 4 in the form of a flexible cast mass, in which the piezoelements 3 are completely embedded, which means to say they are embedded on all sides and in a force-free manner. The cast mass 4 is formed by a curing epoxy resin. On the one hand, the cast mass 4 has such a flexibility and elasticity that the piezoelements 3 which are embedded therein may suitably expand when subjected to voltage, without damaging the cast mass 4, but on the other hand however, the cast mass 4 is so intrinsically stable that it holds the piezoelements 3 in the represented calotte shape.

The piezoelements have an essentially cylindrical shape having an end 10, which is directed to the therapy focus 2 of the transducer 1, as well as an outwardly directed end 11, which is directed away from the focus. The piezoelements 3 are contacted and electrically connected at the ends 10 and 11. Each contacting location 6 at an end side 10 and 11 connects a piezoelement 3 to an electrically conductive wire 7. The piezoelements 3 arranged next to one another are connected in parallel by the wires 7, which is to say that the contacting locations 6 at the inwardly directed ends 10 are on the one hand electrically conductively connected, and the contacting locations 6 at the outwardly directed ends 11 on the other hand are electrically conductively connected. The parallel wires 7 are led as electrical connections 5 laterally out of the transducer 1, in particular out of the cast mass 4. The piezoelements 3 arranged next to one another may be subjected to voltage via the connections 5, indeed for producing shock waves.

The electrical wires 7, which electrically connect the piezoelements 3 to one another, have a diameter of between 0.1 mm and 0.8 mm. They are thus dimensioned such that, on the one hand, they have an adequate conductive cross section, but on the other hand, the movement of the piezoelements 3 is hindered as little as possible when being subjected to voltage. One may also use braided cords or the like, which are highly flexible, instead of the individual wires. Such an arrangement is particularly to be recommended with the activation of the transducer at greater frequencies, in order to counteract a possible skin effect.

Figure 2:
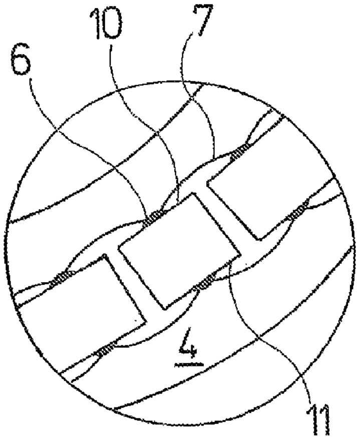
FIG. 2 is an enlarged detail of circled portion II in FIG. 1.

The previously described embodiment represented by FIGS. 1 and 2 shows a transducer in calotte shape, but it is to be understood that this is only a basic representation. The transducer 1 may be designed in practically every and any spatial shape, as well as planar transducers according to the previously described construction principle.

Another embodiment of a transducer according to the invention is represented by FIGS. 3 and 4, with which quasi a backing is provided, as is known per se with transducer calottes having a carrier according to the prior art. The backing here is formed by a rear-side reinforcement of each individual piezoelement 3, specifically by a reinforcement body 8 which is attached on the end 11 which faces outwardly, thus the rear side of each piezoelement 3. The reinforcement bodies 8 in the represented embodiment have a cylinder shape and with regard to their outer contour are adapted to the contour of the piezoelements 3. The reinforcement bodies 8 are made of an electrically conductive metal and are electrically conductively bonded on the rear end 11 of the piezoelements 3. The contacting, as is evident from FIG. 4, is effected via contacting locations 6, which are arranged at the free end of the reinforcement body 8. The piezoelements 3 are thus extended in the axis direction by the reinforcement body 8, and the contacting is then effected at the two ends of the thus formed cylinder body, comprising the piezoelement 3 and reinforcement body 8.

Piezoelements 3 and reinforcement bodies 8, including the contacting and wiring, are embedded in the cast mass 4. The reinforcement bodies 8 may be designed in a profiled manner on the peripheral side, for example by groove- or wave-shaped incisions or other suitable surface structures, in order to achieve an intimate interconnection between the cast mass 4 and the reinforcement bodies 8. The reinforcement bodies here are designed as cylinder bodies merely by example. Other suitable body shapes may also be selected, for example truncated cone shape or calotte shape, optionally also in combination, depending on the demand of the shock wave profile of the transducer.

A multi-layer transducer 1 is represented schematically in FIG. 5. There, groups of piezoelements 3 arranged next to one another are embedded into the cast mass 4 in two layers, which lie behind one another with respect to the focus 2. The connection and construction is effected analogously to the design described by FIGS. 1 and 2. The transducer represented in FIG. 5 is constructed in a two-layered manner, thus comprises two groups of piezoelements 3, which are connected in parallel and whose electrical connections are led out in a separate manner, specifically to the connection pair 5, which connects the inner-lying piezoelement group, and to a connection pair 9, which connects the outer-lying piezoelement group.

This arrangement, compared to the comparable prior art (German Patent DE 197 33 233 C1), has the advantage that the groups may be electrically activated in each case individually and have no common connection, as is formed by the metallic calotte body of the prior art.

The embodiments described above illustrate the basic construction of the transducer according to the invention. It is to be understood that a multitude of different transducer construction types may be formed according to this principle, which here have not been described in detail. That is, invention is not limited to the particular embodiments disclosed, but it is intended to cover modifications within the spirit and scope of the present invention as defined by the appended claims.

I claim:

1. An electroacoustic transducer comprising a plurality of piezoelements (3) arranged next to one another, the piezoelements (3) being arranged in a carrier-free manner and embedded in a composite mass (4).

2. The electroacoustic transducer according to claim 1, wherein the composite mass (4) is formed by an elastic cast mass, which is electrically insulating and surrounds the piezoelements (3).

3. The electroacoustic transducer according to claim 2, wherein the elastic cast mass surrounds the piezoelements (3) on all sides.

4. The electroacoustic transducer according to claim 1, wherein the piezoelements (3) are connected via electrically conductive connection wires (7) which contact the piezoelements on their ends, and wherein the piezoelements are connected in parallel.

5. The electroacoustic transducer according to claim 4, wherein the connection wires (7) have a diameter between 0.1 mm to 0.8 mm and are integrated in the composite mass (4).

6. An electroacoustic transducer comprising:

a plurality of piezoelements (3) arranged next to one another, the piezoelements (3) being arranged in a carrier-free manner and embedded in a composite mass (4), wherein each piezoelement (3) is provided with a rear-side reinforcement (8), which is likewise embedded in the composite mass (4).

7. The electroacoustic transducer according to claim 6, wherein the rear-side reinforcement (8) together with its associated piezoelement (3) is surrounded on all sides with the composite mass (4).

8. The electroacoustic transducer according to claim 6, wherein the rear-side reinforcement (8) is formed by a reinforcement body which is bonded on a rear end (11) of the piezoelement (3).

9. The electroacoustic transducer according to claim 6, wherein the reinforcement body (8) is electrically conductive.

10. The electroacoustic transducer according to claim 9, wherein the reinforcement body (8) comprises metal and is connected to one side of its associated piezoelement (3) in an electrically conductive manner.

11. The electroacoustic transducer according to claim 10, wherein the electrical connection of the reinforcement body (8) and the associated piezoelement (3) is effected at a side of the reinforcement body (8) facing away from the piezoelement (3).

12. The electroacoustic transducer according to claim 9, wherein the reinforcement body (8) comprises a non-conductive material provided with an electrically conductive layer, which is connected to its associated piezoelement (3) in an electrically conductive manner, and wherein an electrical connection of the plurality of piezoelements (3) is effected via the electrically conductive layer of the reinforcement body (8) at a side of the reinforcement body (8) facing away from the piezoelement (3).

13. The electroacoustic transducer according to claim 12, wherein the non-conductive material is selected from glass, ceramic and composites.

14. The electroacoustic transducer according to claim 6, wherein the reinforcement body (8) has a shape selected from cylindrical, conical, truncated cone, and hemispherical.

15. The electroacoustic transducer according to claim 1, wherein the plurality of piezoelements (3) are arranged next to one another in an a shape selected from a plane, spatially curved in a single-axis manner, and spatially curved in a two-axis manner.

16. The electroacoustic transducer according to claim 1, wherein groups of piezoelements (3) arranged next to one another are arranged behind one another with a spacing and embedded in the composite mass (4), and wherein the piezoelements of each group are electrically connected independently of piezoelements of each other group.

17. An apparatus for medical shock-wave treatment, the apparatus comprising an electroacoustic transducer according to claim 1.

* * * * *